July 4, 1950 F. MEILLAND Plant Pat. 959
ROSE PLANT
Filed April 4, 1949
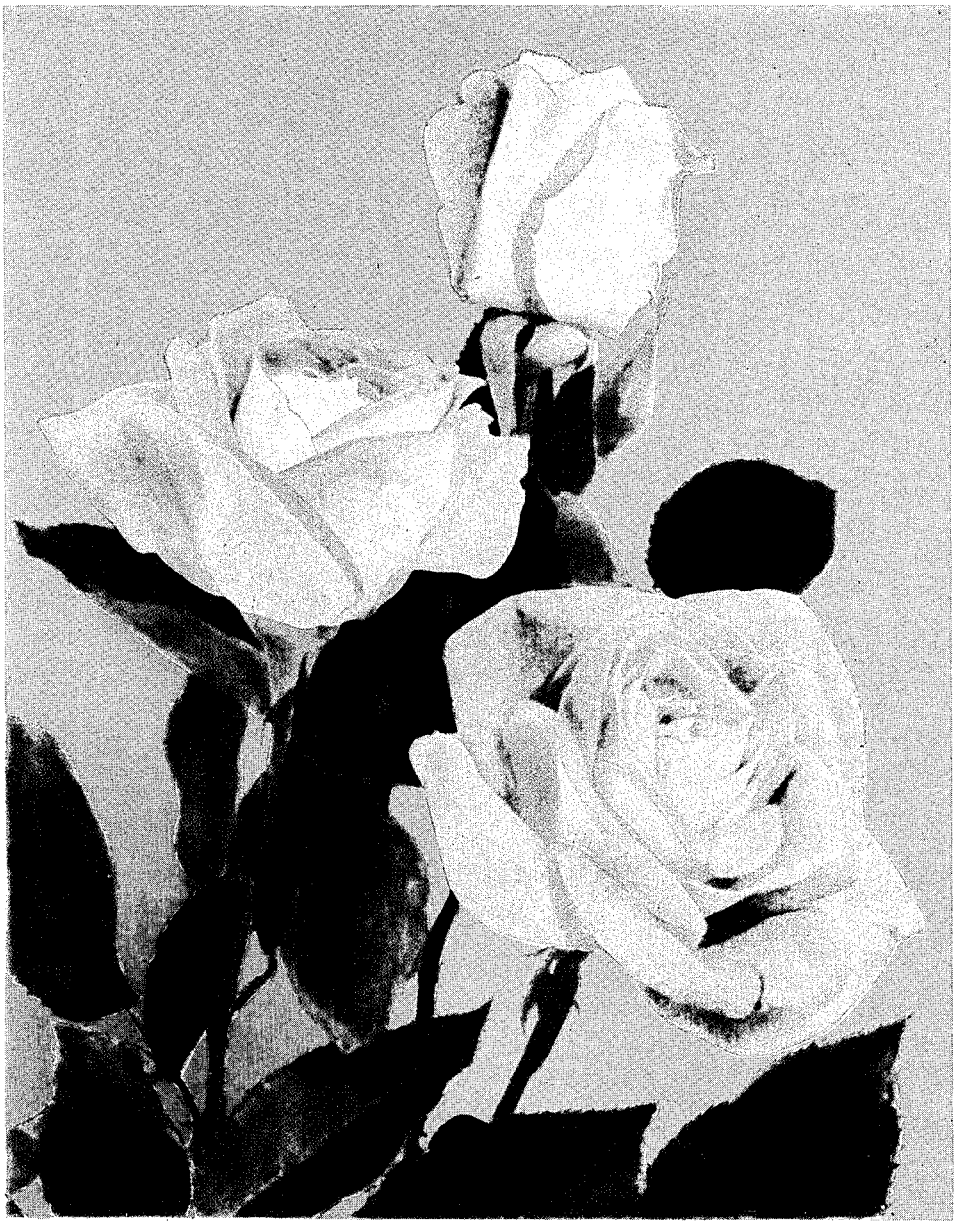
Inventor
F. Meilland
By Robbins & Robbins
by H. C. Robbins
attorneys.

Patented July 4, 1950

Plant Pat. 959

UNITED STATES PATENT OFFICE

959

ROSE PLANT

Francis Meilland, Cap Azura, Cap d'Antibes, France, assignor to The Conard-Pyle Company, West Grove, Pa., a corporation of Pennsylvania Application April 4, 1949, Serial No. 85,398

1 Claim. (Cl. 47—61)

The present invention relates to a new and distinct variety of rose plant, resulting from careful efforts of cross breeding to obtain certain combinations of characteristics both in respect to habits of growth and color of blooms.

This new variety is characterized as to novelty dominantly by the extraordinarily vivid and contrasting colors of the flowers, involving a new combination of color tones. Also, the variety is notable for the glossiness of its foliage and the vigorous growth of the plant.

Asexual reproduction of this new variety by budding at Tassin-les-Lyon, Rhone, France, and at West Grove, Pennsylvania, shows the foregoing characteristics come true to form and are established.

In the drawings are illustrated specimens of this new variety, depicting the flowers at different stages of development from closed bud to full blown flower.

The following is a detailed description of the new variety, all reference to color being in accordance with Ridgway's Color Standards and Nomenclature:

Type: Hardy; bush; outdoor; seedling; for cut flowers and garden decoration.

Class: Hybrid tea.

Breeding: Seedling. ("Mme. Joseph Perraud" × "Brasier") × ("Charles P. Kilham" × "Capucine Chambard"). (The foregoing varieties are all unpatented.)

Propagation: Holds its distinguishing characteristics through succeeding propagations by budding.

*Flower*

Locality where grown: West Grove, Pennsylvania.

Flowers borne: Singly or rarely two or three to stem; on normally strong, medium long stems.

Quantity of bloom: Free to abundant outdoors.

Continuity: Continuous.

Fragrance: Penetrating; tea.

Bud:

*Peduncle.*—Medium length; medium heavy; erect; almost smooth; few red brown prickles. Color—Lettuce Green, Plate V, frequently shaded with Walnut Brown, Plate XXVIII.

*Before calyx breaks.*—Size—medium large. Form—pointed; with foliaceous appendages on the surface of the bud; with slender cut foliaceous parts extending beyond the tip of the bud equal to one-fourth of its length.

*As calyx breaks.*—Color—shading from Lemon Chrome, Plate IV, to Empire Yellow, Plate IV, with streaks and tinges of Nopal Red, Plate I, and shading to Light Viridine Yellow, Plate V, at apex.

*As first petal opens.*—Size—medium. Form—medium long; pointed. Color—outside: shading from bright Empire Yellow, Plate IV, at base to Apricot Yellow, Plate IV, and to Orange Buff, Plate III, occasionally with tinges of Rose Doree, Plate I, near outer edge; inside: shading from bright yellowish Lemon Chrome, Plate IV, at base to dark velvety Spectrum Red, Plate I, over more than one-half the petal surface, occasionally with thin yellowish streaks along midrib.

*Opening.*—Opens up well.

Bloom: Size, when fully open—large; four inches to five inches.

*Petalage.*—Double; from 25 to 35 petals; arranged regularly.

*Form.*—High center at first; remaining high centered; petals remaining at first loosely cupped inward; becoming later, at maturity, very loosely rolled outward.

Petals: Thick; with inside velvety and outside satiny.

*Shape.*—Outside—obovate. Intermediate—obovate. Inside—obovate.

*Color.*—Colors may be modified by being striped and shaded with other colors.

This description of a newly opened flower was made from a rose grown outdoors in the month of August, at West Grove, Pennsylvania:

*Color.*—*Outside petal*—outside surface: Shading from Pinard Yellow, Plate IV, at base to Maize Yellow, Plate IV; inside surface—shading from Lemon Yellow, Plate IV, at base to Empire Yellow, Plate IV, shading or streaking to Strawberry Pink, Plate I, and to Rose Red, Plate XII, with streaks of Baryta Yellow, Plate IV, near midrib. *Intermediate petal*—outside surface: shading from Empire Yellow, Plate IV, at base to Maize Yellow, Plate IV, at base; inside surface: shading from Lemon Chrome, Plate IV, at base to Apricot Yellow, Plate IV, shading or streaking to Strawberry Pink, Plate I, and to Rose Red, Plate XII, over about two-thirds of petal surface. *Inner petal*—outside surface: shading from bright Empire Yellow, Plate IV, to Buff Yellow, Plate IV; inside surface:

shading from Lemon Chrome, Plate IV, at base to Scarlet Red, Plate I, to bright Spectrum Red, Plate I, over about five-sixths of petal surface, occasionally with streaks of Pale Lemon Yellow, Plate IV, down midrib.

This description was made from a rose that was open for three days outdoors in the month of August, at West Grove, Pennsylvania:

*Color.—Outside petal* — outside surface: shading from bright Amber Yellow, Plate XVI, at base to Maize Yellow, Plate IV; inside surface—shading from Lemon Chrome, Plate IV, at base to Rose Red, Plate XII, over about three-fourths of petal surface; sometimes shading to dark Rhodamine Purple, Plate XII, or light Rosolane Purple, Plate XXVI, over three-fourths of petal surface. *Inside petal*—Outside surface: shading from bright Pinard Yellow, Plate IV, to Maize Yellow, Plate IV; inside surface: shading from Picric Yellow, Plate IV, at base to Rose Red, Plate XII, over about two-thirds of petal surface; sometimes shading to Rose Doree, Plate I, or Spinel Pink, Plate XXVI.

*General color effect.*—Newly opened flower—Buff Yellow, Plate IV, and Rose Red, Plate XII. Three days open—Rose Red, Plate XII, occasionally showing shades of Light Rosolane Purple, Plate XXVI, or Rosolane Purple, Plate XXVI.

*Behavior.*—Drop off cleanly.

*Flower longevity.*—Cut roses grown outdoors kept at living-room temperatures—4 to 5 days in August.

*Reproductive organs*

Stamens: Medium number; arranged regularly about pistils.

Filaments: Medium length; most with anthers. Color—Peach Red, Plate I, to Jasper Red, Plate XIII.

Anthers: Medium side; occasionally an anther fused with a petaloid or a pistil. Color—Deep Chrome, Plate III, with Pale Orange-Yellow center stripe.

Pollen: Moderately abundant. Color—Light Cadmium, Plate IV.

Pistils: Medium number.

Styles: Uneven; medium length; medium heavy; bunched.

Stigma: Color—Empire Yellow, Plate IV.

Ovaries: Some protruding from calyx.

Hips: Ovoid to globular; smooth; walls moderately thick. Color—Lettuce Green, Plate V.

Sepals: Permanent; medium length; spear-shaped.

Seeds: Medium number; medium large.

*Plant*

Foliage:

*Leaves.*—Compound of three or five leaflets; normally abundant; small to medium; leathery.

*Leaflets.*—Shape, ovoid with apex acute; base round; margin simply serrate.

*Color.—Mature*—upper surface: Dark Cress Green, Plate XXXI; under surface: Asphodel Green, Plate XLI. *Young*—upper surface: Yellowish Oil Green, Plate XXX, veiled and edged with Indian Red, Plate XXVII; under surface: Indian Red, Plate XXVII, to Mineral Red, Plate XXVII.

*Rachis.*—Medium heavy. Upper side—grooved. Under side—sparsely thorny.

*Stipules.*—Medium length; medium width; with medium length points turning out at an angle of less than 90°.

Disease: Resistant to mildew; some resistance to blackspot.

Growth:

*Habit.*—upright; branched.

*Growth.*—vigorous.

*Canes.*—heavy.

*Main stems.*—Color, reddish green. *Thorns*—several; long; hooked downward; with medium narrow base; several very small incipient thorns among large thorns. *Prickles*—several; green-brown. *Hairs*—none.

*Branches.*—Color, dark red. *Thorns*—several; medium length; hooked downward; with short narrow base. *Prickles*—several; reddish. *Hairs*—none.

*New shoots.*—Color, Mignonette Green, Plate XXXI, occasionally covered with Indian Red, Plate XXVII. *Thorns*—several; medium length; hooked downward; with narrow base. Incipient thorns among larger thorns. *Prickles*—several; green-brown. *Hairs*—none.

I claim:

A new and distinct variety of rose plant characterized as to novelty by the extraordinarily vivid and contrasting colors of the flowers, producing a new combination of color tones in roses of its class, the glossy disease resistant foliage, and vigorous growing habit of the plant, substantially as shown and described.

FRANCIS MEILLAND.

No references cited.